(12) United States Patent
Omiya et al.

(10) Patent No.: US 10,145,765 B2
(45) Date of Patent: Dec. 4, 2018

(54) METHOD OF SUPPRESSING BACKGROUND RISE IN COLOR REAGENT SOLUTION, COLOR REAGENT SOLUTION, REAGENT KIT, AND MEASURING APPARATUS

(71) Applicant: ARKRAY, Inc., Kyoto (JP)

(72) Inventors: Kazuhiro Omiya, Kyoto (JP); Toshihiro Imai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/665,408

(22) Filed: Mar. 23, 2015

(65) Prior Publication Data

US 2015/0276561 A1 Oct. 1, 2015

(30) Foreign Application Priority Data

Mar. 26, 2014 (JP) .................... 2014-062845

(51) Int. Cl.
  *G01N 31/22* (2006.01)
  *G01N 1/28* (2006.01)
  *G01N 35/10* (2006.01)
  *G01N 33/84* (2006.01)
  *G01N 35/04* (2006.01)
  *B01L 3/00* (2006.01)

(52) U.S. Cl.
  CPC ............ *G01N 1/28* (2013.01); *G01N 31/228* (2013.01); *G01N 33/84* (2013.01); *G01N 35/1002* (2013.01); *B01L 3/502* (2013.01); *B01L 3/5085* (2013.01); *G01N 2035/0436* (2013.01); *Y10T 436/206664* (2015.01)

(58) Field of Classification Search
  None
  See application file for complete search history.

(56) References Cited

U.S. PATENT DOCUMENTS

| | | | |
|---|---|---|---|
| 6,180,412 B1* | 1/2001 | Kroll | G01N 33/182 422/408 |
| 6,203,579 B1* | 3/2001 | Moeller | A61K 8/492 8/405 |
| 6,355,489 B1 | 3/2002 | Carratelli | |
| 2004/0010862 A1 | 1/2004 | Audousset | |

FOREIGN PATENT DOCUMENTS

| | | |
|---|---|---|
| EP | 0783692 B1 | 11/1998 |
| EP | 1512751 A1 | 3/2005 |
| EP | 2749885 A1 | 7/2014 |
| JP | 2000-095654 A | 4/2000 |
| JP | 2001-181243 A | 7/2001 |
| JP | 2005-274564 A | 10/2005 |
| JP | 2006-347604 A | 12/2006 |
| JP | 2009-257909 A | 11/2009 |
| WO | 01/78667 A1 | 10/2001 |

OTHER PUBLICATIONS

Extended European Search Report issued in corresponding European Patent Application No. 15161027.6 dated Jun. 25, 2015.
Office Action issued in corresponding European Patent Application No. 15161027.6 dated Jun. 30, 2017.
Office Action issued in corresponding Japanese Patent Application No. 2015-056099 dated Oct. 23, 2018.

* cited by examiner

*Primary Examiner* — Paul S Hyun
(74) *Attorney, Agent, or Firm* — Morgan, Lewis & Bockius LLP

(57) ABSTRACT

A method is provided for suppressing, in a color reagent solution which is used to measure a component within a sample and which contains an oxidative color reagent dissolved therein, a background rise that occurs when the color reagent solution is stored. The method includes adjusting a hydrogen ion exponent (pH) of the color reagent solution so as to be strongly acidic. The hydrogen ion exponent is preferably adjusted to 2.9 or below or to 2.1 or below. The color reagent solution is preferably used to measure the degree of oxidative stress. The oxidative color reagent is preferably a phenylenediamine derivative.

9 Claims, 10 Drawing Sheets

| PLACE | CONTENTS | AMOUNT CHARGED |
|---|---|---|
| SAMPLE CHAMBER 10 | SAMPLE S | 50 μL |
| COLOR REAGENT SOLUTION CHAMBER 11 | COLOR REAGENT SOLUTION RS1 | 200 μL |
| PHOTOMETRIC CELL 12 | --- | --- |
| DILUTING CHAMBER 13 | --- | --- |
| DILUTING FLUID CHAMBER 14 | DILUTING FLUID RS4 | 400 μL |
| CLEANING FLUID CHAMBER 15 | CLEANING FLUID RS5 | 400 μL |
| TIP LOADING STATION 16 (WASTE CHAMBER) | TIP 17 | --- |

FIG. 3
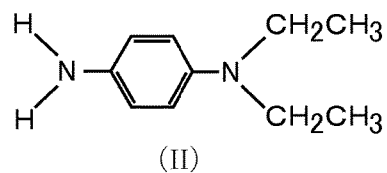
(II)
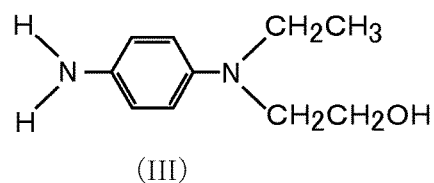
(III)
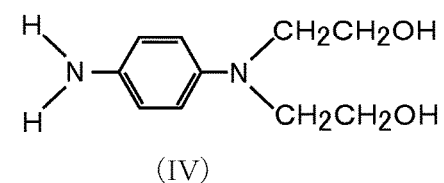
(IV)
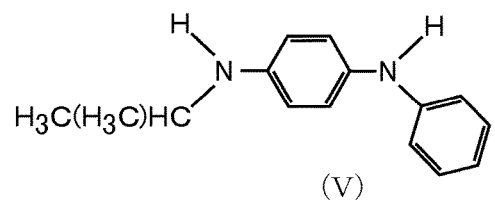
(V)
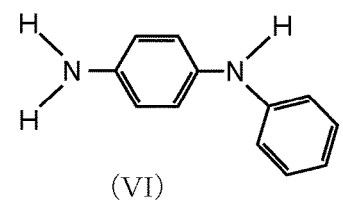
(VI)
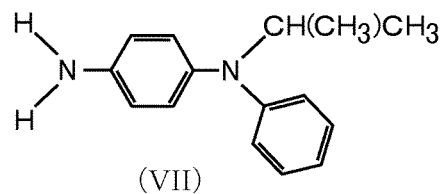
(VII)
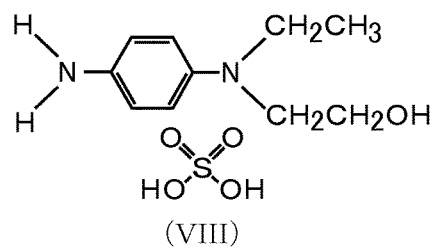
(VIII)
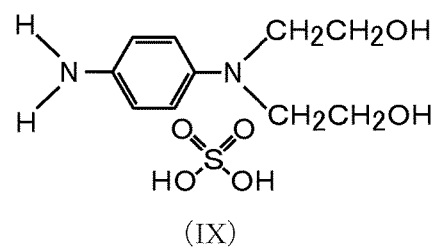
(IX)
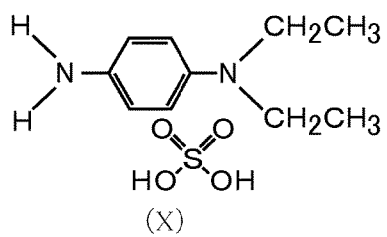
(X)

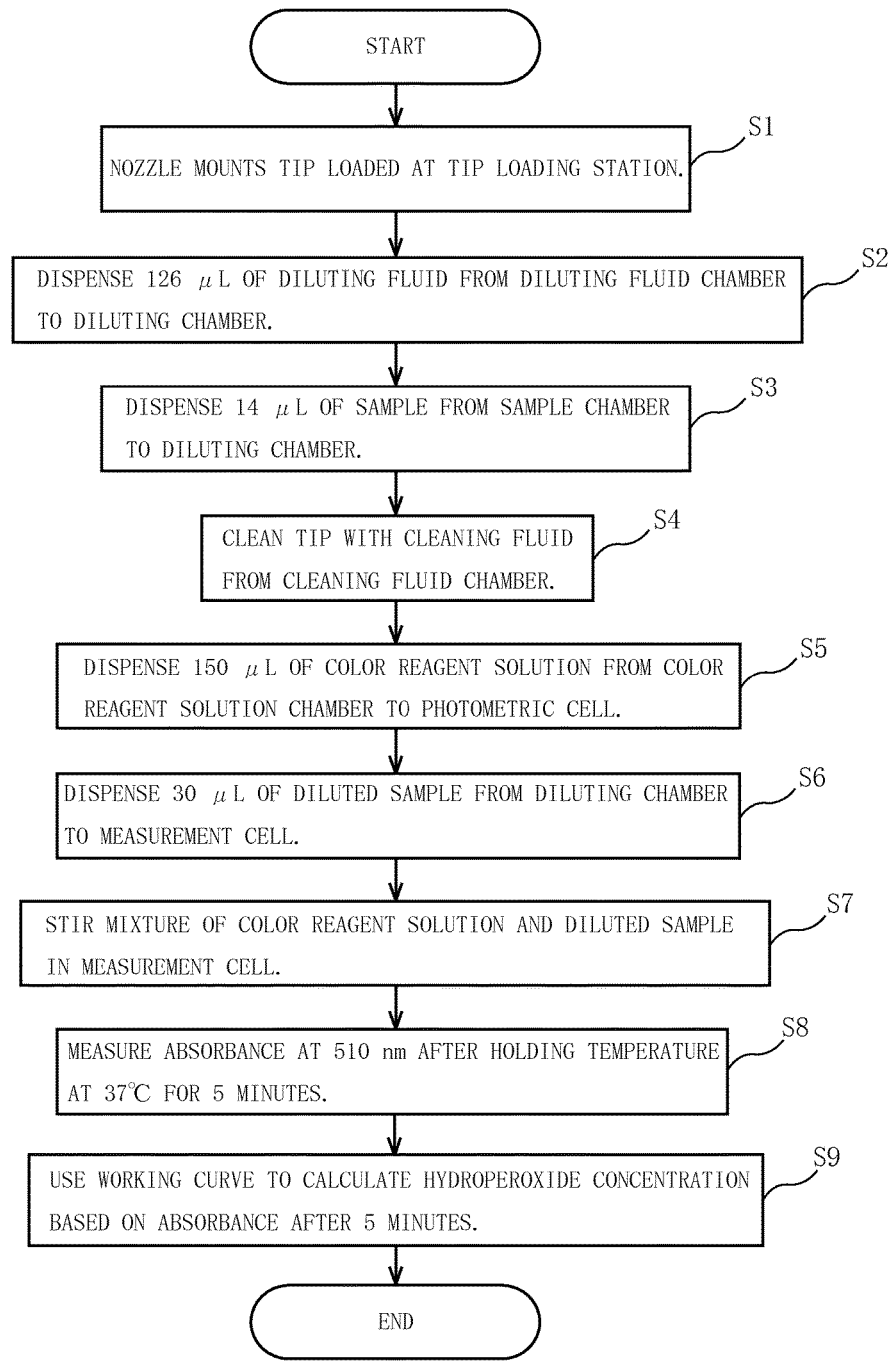

FIG. 5

FORMULATION IN EXAMPLE 1

|  | OXIDATIVE COLOR REAGENT | STRONG ACID |
|---|---|---|
| COMPARATIVE COLOR REAGENT SOLUTION (1) | N,N-BIS(2-HYDROXYETHYL)-1,4-PHENYLENEDIAMINE SULFATE, 3.2 mM | -- |
| COMPARATIVE COLOR REAGENT SOLUTION (2) | N-ETHYL-N-(2-HYDROXYETHYL)-1,4-PHENYLENEDIAMINE SULFATE, 3.2 mM | -- |
| COLOR REAGENT SOLUTION (1) | N,N-BIS(2-HYDROXYETHYL)-1,4-PHENYLENEDIAMINE SULFATE, 3.2 mM | SULFURIC ACID, 0.1 M |
| COLOR REAGENT SOLUTION (2) | N-ETHYL-N-(2-HYDROXYETHYL)-1,4-PHENYLENEDIAMINE SULFATE, 3.2 mM | SULFURIC ACID, 0.1 M |

FIG. 6

CONFIRMATORY RESULTS FOR EXAMPLE 1

|  | IMMEDIATELY AFTER PREPARATION | ON DAY 14 AT 40°C |
|---|---|---|
| COMPARATIVE COLOR REAGENT SOLUTION (1) | CLEAR | VIOLET |
| COMPARATIVE COLOR REAGENT SOLUTION (2) | CLEAR | VIOLET |
| COLOR REAGENT SOLUTION (1) | CLEAR | SLIGHTLY PINK |
| COLOR REAGENT SOLUTION (2) | CLEAR | CLEAR |

FIG. 7

FORMULATION IN EXAMPLE 1

|  | STRONG ACID | pH | | | |
|---|---|---|---|---|---|
| COMPARATIVE COLOR REAGENT SOLUTION (3) | NONE | -- | -- | -- | -- |
| COLOR REAGENT SOLUTION (3) | SULFURIC ACID | 1.9 | 2.2 | 2.6 | -- |
| COLOR REAGENT SOLUTION (4) | HYDROCHLORIC ACID | 2.0 | 2.6 | 2.7 | 2.8 |
| COLOR REAGENT SOLUTION (5) | LACTIC ACID | 2.1 | 2.4 | 2.5 | -- |
| COLOR REAGENT SOLUTION (6) | ACETIC ACID | 1.9 | 2.4 | 2.7 | 2.9 |
| COLOR REAGENT SOLUTION (7) | PROPIONIC ACID | 2.0 | 2.5 | 2.7 | 2.9 |
| COLOR REAGENT SOLUTION (8) | p-TOLUENESULFONIC ACID | 2.0 | 2.4 | 2.8 | 2.9 |

OXIDATIVE COLOR REAGENT: N,N-BIS(2-HYDROXYETHYL)
-1,4-PHENYLENEDIAMINE SULFATE, 3.2 mM

FORMULATION IN EXAMPLE 3

|  | OXIDATIVE COLOR REAGENT | STRONG ACID |
|---|---|---|
| COMPARATIVE COLOR REAGENT SOLUTION (4) | N,N-BIS(2-HYDROXYETHYL)-1,4-PHENYLENEDIAMINE SULFATE, 3.2 mM | -- |
| COLOR REAGENT SOLUTION (9) | N,N-BIS(2-HYDROXYETHYL)-1,4-PHENYLENEDIAMINE SULFATE, 3.2 mM | p-TOLUENESULFONIC ACID, 0.1 M |

EXAMPLE 3: CONFIRMATION OF REACTIVITY

METHOD OF SUPPRESSING BACKGROUND RISE IN COLOR REAGENT SOLUTION, COLOR REAGENT SOLUTION, REAGENT KIT, AND MEASURING APPARATUS

BACKGROUND OF THE INVENTION

1. Field of the Invention

This invention relates to a method of suppressing a background rise in a color reagent solution which is used to measure a component within a sample and which contains an oxidizing color reagent dissolved therein. The invention further relates to a color reagent solution which is used to measure a component within a sample and which contains an oxidizing color reagent dissolved therein, a reagent kit which includes such a color reagent solution, and a measuring apparatus which carries out measurement using such a reagent kit.

2. Description of the Related Art

It is generally held that about 2% of the oxygen consumed within an organism changes into reactive oxygen/free radicals. Here, "reactive oxygen/free radical" refers to a chemical species which is both reactive oxygen and a free radical. Most such reactive oxygen/free radicals are destroyed by the action of antioxidants and antioxidant enzymes; the reactive oxygen/free radicals that are not destroyed oxidize biological components such as DNA, lipids, enzymes and protein. It has been shown that oxidative damage to these biocomponents promotes aging and is also associated with the onset of diseases such as diabetes, high blood pressure and arteriosclerosis.

Here, the balance between reactive oxygen/free radicals on one hand and antioxidants and antioxidant enzymes on the other is referred to as the "oxidative stress." The extent of such oxidative stress is referred to as the "degree of oxidative stress." A "high oxidative stress" means that the balance within the organism between oxidizing effects by reactive oxygen/free radicals and antioxidizing effects by antioxidants and the like has broken down, resulting in state where there is a rise in oxidizing reactions. A state where the degree of oxidative stress is high is a state that is undesirable to the organism.

European Patent No. 0783692 B1, U.S. Pat. No. 6,355, 489 B1 and Japanese Patent Application Laid-open No. 2009-257909 disclose methods for measuring the degree of oxidative stress. Components such as lipids, proteins, amino acids and nucleic acids within an organism incur oxidative reactions under the effect of reactive oxygen/free radicals, becoming hydroperoxides (R—OOH). These hydroperoxides are thus capable of serving as markers of the degree of oxidative stress. In the measurement methods described in these patent publications, the reactive oxygen/free radicals that arise within an organism are not directly measured; instead, the concentration of hydroperoxides within the blood that have formed under the action of the reactive oxygen/free radicals is measured using a color reaction, and the degree of oxidative stress within the organism is collectively assessed.

In the foregoing patent literature, p-phenylenediamine derivatives, which are oxidative color reagents, are used as the color reagents for such color reactions. These p-phenylenediamine derivatives are characterized by having a high sensitivity, and are useful as color reagents for use in measuring the concentration of such hydroperoxides.

However, there remains room for further improvement in the existing art.

That is, oxidative color reagents such as p-phenylenediamine derivatives are relatively unstable in a solution state and have a tendency to react with oxygen in the solution, as a result of which unintended coloration readily arises. On account of this, when stored in a solution state, a rise in the background occurs. One solution has been to, for example, freeze-dry the oxidative color reagent and store it as a dry reagent. This dry reagent is dissolved with a dissolving fluid at the time of use, and furnished for use. However, the need for such a pretreatment operation at the time of use is a burden on the operator who carries out the measurement. Hence, it would be desirable for the oxidative color reagent to be capable of being stored in a liquid state.

SUMMARY OF THE INVENTION

It is therefore an object of this invention to provide a method of suppressing, in a color reagent solution which is used to measure a component within a sample and which contains an oxidative color reagent dissolved therein, a background rise that occurs when the color reagent solution is stored. Further objects of the invention are to provide a color reagent solution which is used to measure a component within a sample and which contains an oxidizing color reagent dissolved therein, a reagent kit which includes such a color reagent solution, and a measuring apparatus which carries out measurement using such a reagent kit.

This invention provides the following technical means for resolving the above problems.

In a first aspect, the invention provides a method of suppressing, in a color reagent solution which is used to measure a component within a sample and which contains an oxidative color reagent dissolved therein, a background rise that occurs when the color reagent solution is stored, this method including adjusting a hydrogen ion exponent of the color reagent solution so as to be strongly acidic.

In the adjustment step, the hydrogen ion exponent of the color reagent solution preferably is adjusted to 2.9 or below or to 2.1 or below.

The color reagent solution is preferably adapted for use in measuring a degree of oxidative stress.

The oxidative color reagent is preferably a phenylenediamine derivative.

The phenylenediamine derivative is preferably a p-phenylenediamine derivative.

The p-phenylenediamine derivative is preferably selected from among compounds represented by general formula (I) below:

[Chem. 1]

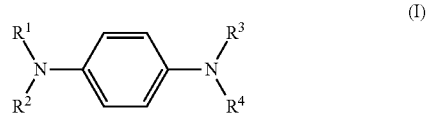

(where $R^1$, $R^2$, $R^3$ and $R^4$ are each independently a hydrogen atom, a methyl group, an ethyl group, an isopropyl group, a hydroxyalkyl group of 1 to 4 carbons, a phenyl group or a halogen group) and salts thereof.

In a second aspect, the invention provides a color reagent solution which is used to measure a component within a sample and contains an oxidative color reagent dissolved therein, wherein the hydrogen ion exponent of the solution has been adjusted so as to be strongly acidic.

In the color reagent solution, the hydrogen ion exponent preferably has been adjusted to 2.9 or below or to 2.1 or below.

The color reagent solution is preferably used to measure a degree of oxidative stress.

The oxidative color reagent is preferably a phenylenediamine derivative.

The phenylenediamine derivative is preferably a p-phenylenediamine derivative.

The p-phenylenediamine derivative is preferably selected from among compounds represented by general formula (I) below:

[Chem. 1]

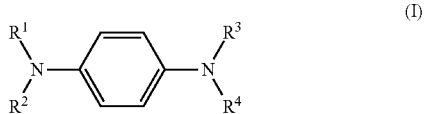

(I)

(where $R^1$, $R^2$, $R^3$ and $R^4$ are each independently a hydrogen atom, a methyl group, an ethyl group, an isopropyl group, a hydroxyalkyl group of 1 to 4 carbons, a phenyl group or a halogen group) and salts thereof.

In a third aspect, the invention provides a reagent kit for use in measuring a component in a sample, this kit including the color reagent solution according to the second aspect of the invention.

Preferably, the reagent kit further includes a diluting fluid for diluting the color reagent solution, wherein the diluting fluid is adjusted with a buffer to a predetermined hydrogen ion exponent suitable for a color reaction, and the color reagent solution exhibits a hydrogen ion exponent that, with dilution of the color reagent solution by the diluting fluid, changes to the predetermined hydrogen ion exponent of the diluting fluid.

In a fourth aspect, the invention provides a measuring apparatus for use in measuring a component of a sample, this apparatus carrying out measurement using the reagent kit according to the third aspect of the invention.

By employing an embodiment of the invention, a background rise in the reagent color solution which is used in the measurement of a component within a sample and which contains dissolved therein an oxidative color reagent can be suppressed. As a result, it is possible to store the oxidative color reagent in a solution state. Therefore, when carrying out the measurement of a component in a sample, the task of dissolving an oxidative color reagent can be eliminated, which is convenient for the operator carrying out the measurement.

Other distinctive features and advantages of the invention shall become apparent from the embodiments of the invention described below in conjunction with the appended diagrams.

BRIEF DESCRIPTION OF THE DRAWINGS

FIG. 3 is a diagram showing examples of the oxidative color reagent which is dissolved within the color reagent solution that has been filled into the cartridge of the measurement system shown in FIG. 1;

FIG. 4 is a flow chart depicting an example of the sequence of operations carried out by the measurement system shown in FIG. 1;

FIG. 5 is a table showing the formulation used in Example 1;

FIG. 6 is a table showing the confirmatory results obtained in Example 1;

FIG. 7 is a table showing the formulation used in Example 2;

DESCRIPTION OF THE PREFERRED EMBODIMENTS

Preferred embodiments of the invention are described below while referring to the diagrams. In this specification, ranges in numerical values indicated as "from A to B" indicate a range in numerical values where A is the minimum value and B is the maximum value in the range. Also, in the description that follows, directions such as the vertical direction are as shown in the diagrams.

Measurement System

Figure 1:
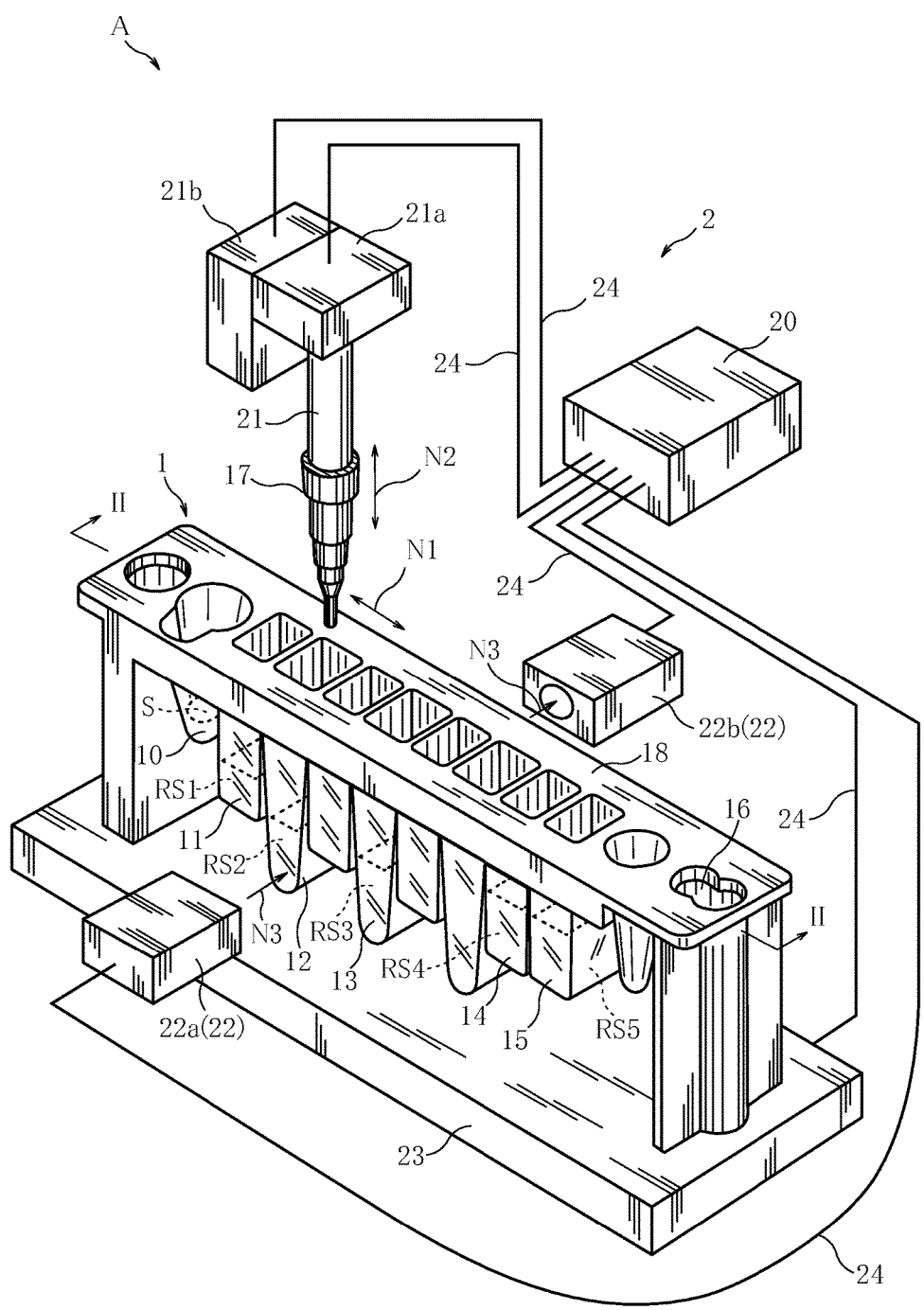
FIG. 1 is a perspective view schematically showing an exemplary configuration of a measurement system equipped with a cartridge containing a color reagent solution according to the invention and a measuring apparatus for carrying out measurement on the cartridge.

FIG. 1 shows an example of a measurement system which includes a color reagent solution according to the invention, a cartridge containing this color reagent solution, and a measuring apparatus for measuring the degree of oxidative stress within an organism using this cartridge. The measurement system A is provided with a cartridge 1 and a measuring apparatus 2. The cartridge 1 is set in a small measuring apparatus 2 installed at, for example, a clinic or a hospital ward, and is used to measure the amount of a component within a sample S. The component within the sample S may be, for example, a hydroperoxide (R—OOH). The hydroperoxide is a product that has formed as a result of the oxidation of a lipid, protein, amino acid, nucleic acid or the like within the organism by reactive oxygen/free radicals. The hydroperoxide concentration obtained by measurement can be used to collectively assess the degree of oxidative stress within the organism. The sample S is exemplified by biological samples such as whole blood, blood plasma, blood serum, urine, saliva, and interstitial fluid. These samples S may be used as is or may be used after dilution with a diluting fluid RS4.

Cartridge

Figure 2:
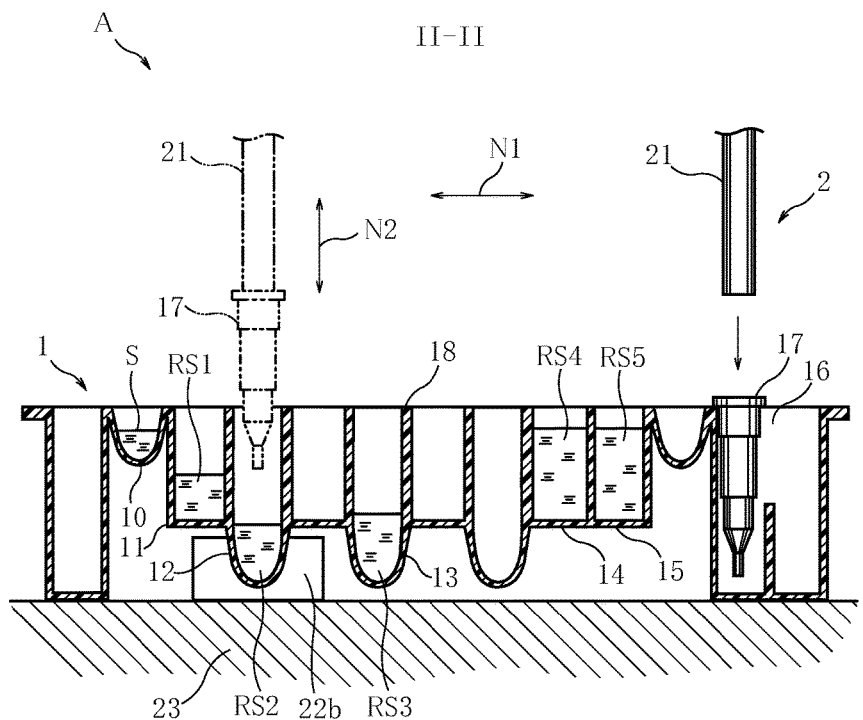
FIG. 2 is a cross-sectional view, along line II-II, of the measurement system shown in FIG. 1.
Figure 8:
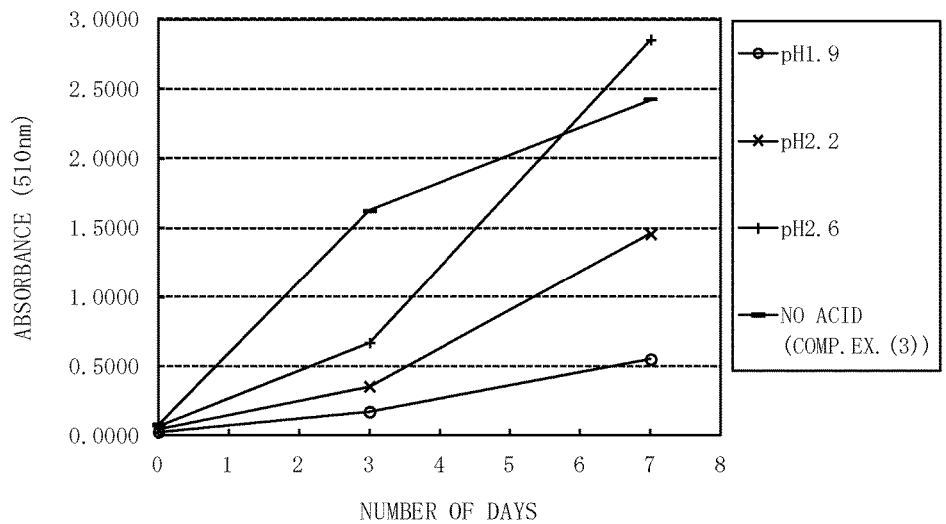
FIG. 8 is a graph showing the confirmatory results obtained for Color Reagent Solution (3) in Example 2.
Figure 9:
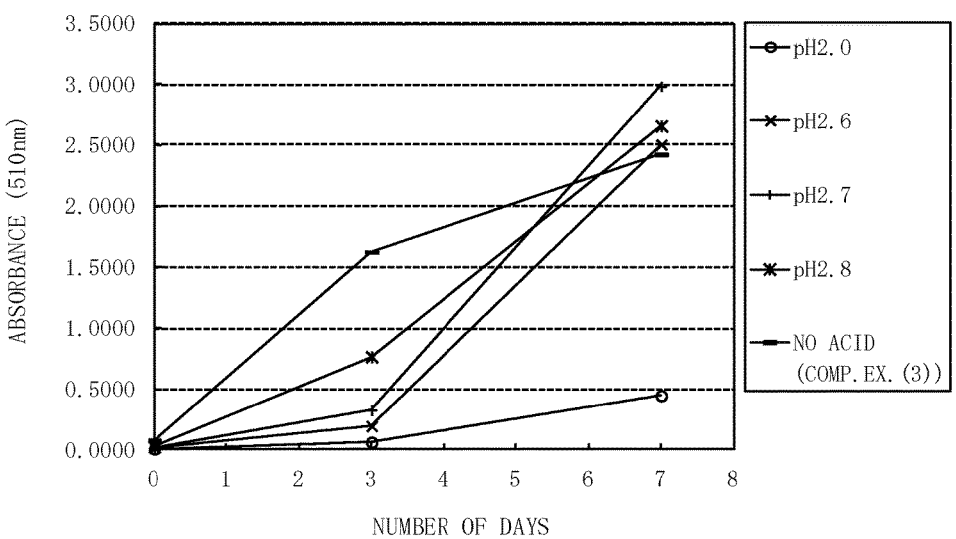
FIG. 9 is a graph showing the confirmatory results obtained for Color Reagent Solution (4) in Example 2.
Figure 10:
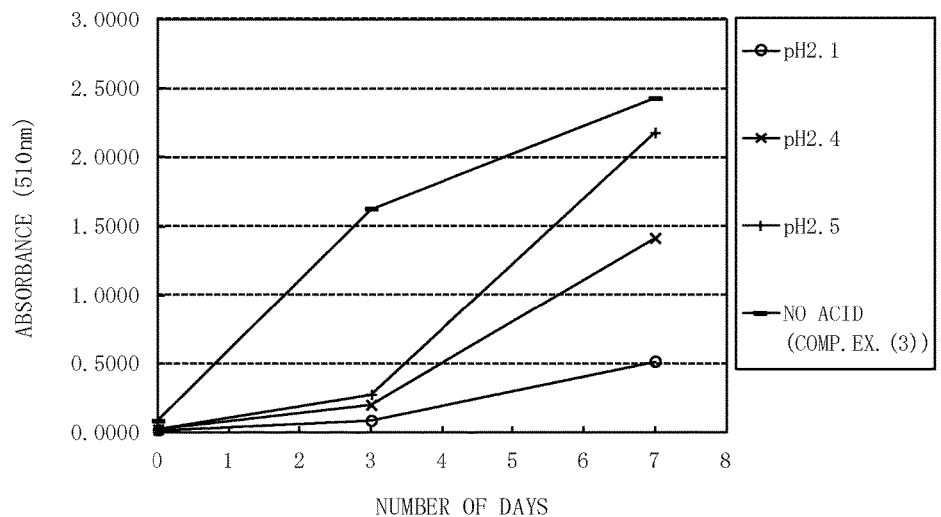
FIG. 10 is a graph showing the confirmatory results obtained for Color Reagent Solution (5) in Example 2.
Figure 11:
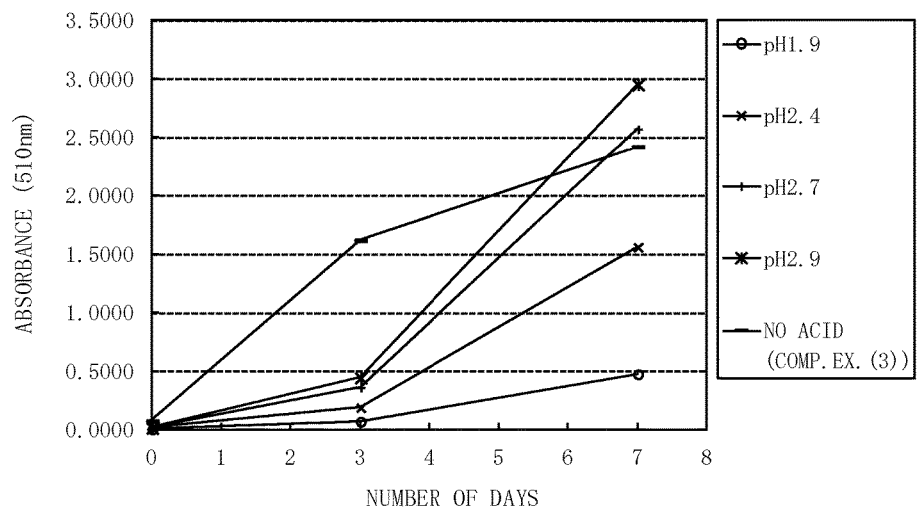
FIG. 11 is a graph showing the confirmatory results obtained for Color Reagent Solution (6) in Example 2.
Figure 12:
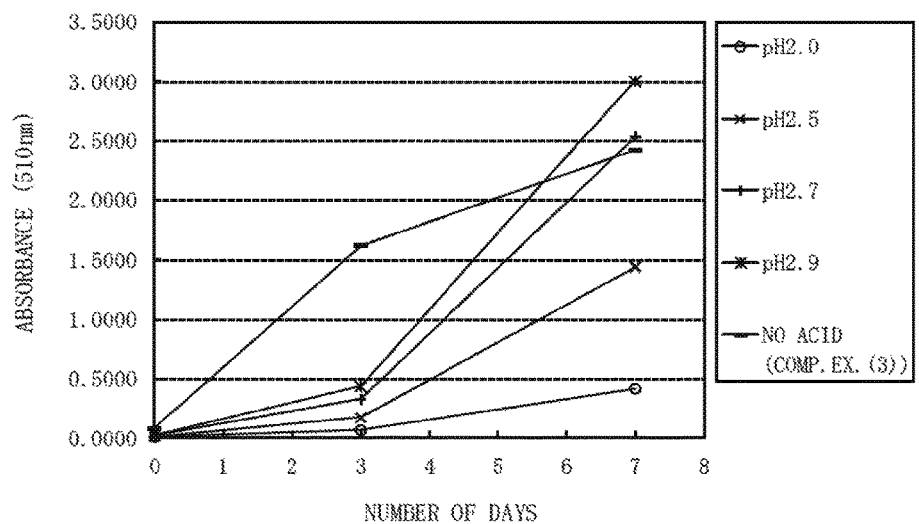
FIG. 12 is a graph showing the confirmatory results obtained for Color Reagent Solution (7) in Example 2.
Figure 13:
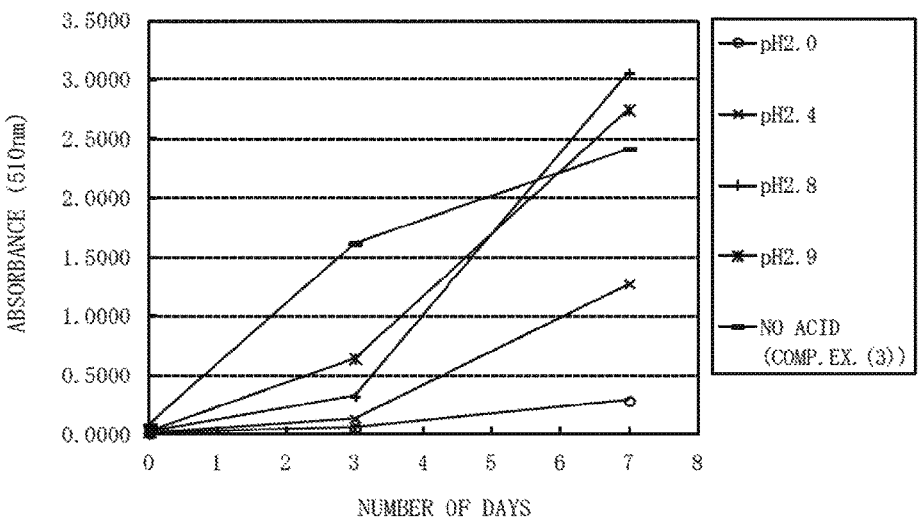
FIG. 13 is a graph showing the confirmatory results obtained for Color Reagent Solution (8) in Example 2.

As shown in FIGS. 1 and 2, the cartridge 1 is a monolithic structure that includes a plurality of chambers, a photometric cell and a tip loading station. This cartridge 1 serves as an embodiment of the reagent kit in the invention. The cartridge 1 is produced by injection-molding, for example, polystyrene as the material. The cartridge 1 allows visible light or ultraviolet light to pass through the photometric cell 12. Accordingly, in addition to polystyrene, use may be made of polymethyl methacrylate (PMMA), polyethylene terephthalate (PET), polycarbonate or the like as the material for the cartridge 1. The cartridge 1 includes all the reagents needed to measure the hydroperoxide concentration. Following production, the cartridge 1 is transported and stored under refrigeration. The refrigeration conditions may be, for example, a temperature of 4° C. or below.

The cartridge 1 has a sample chamber 10, a color reagent solution chamber 11, a photometric cell 12, a diluting chamber 13, a diluting fluid chamber 14, a cleaning fluid chamber 15, and a tip loading station 16. A seal (not shown) is attached to a top surface 18 of the cartridge 1. This seal is an aluminum seal or is made of a multilayer film provided with an aluminum foil or of a synthetic resin film, and covers at least the color reagent solution chamber 11, the diluting fluid chamber 14 and the cleaning fluid chamber 15.

The sample chamber 10 is a chamber for dispensing a sample S. At the time of measurement, the operator uses a pipette or the like to dispense the sample S into the sample chamber 10. The sample S is dispensed in an amount of, for example, 50 µL. The color reagent solution chamber 11 is a chamber for charging and storing the color reagent solution RS1 in which the oxidative color reagent is dissolved. The color reagent solution chamber 11 is charged with, for example, 200 µL of color reagent solution RS1. The photometric cell 12 is a cell for receiving a measurement fluid RS2 obtained by mixing together the color reagent solution RS1 and the sample S, and measuring the coloration that arises due to an oxidizing reaction on the oxidative color reagent. The diluting chamber 13 is a chamber for diluting the sample S with a diluting fluid RS4 to form a diluted sample RS3. The diluting fluid chamber 14 is a chamber for charging the diluting fluid RS4 used to dilute the sample S. The diluting fluid chamber 14 functions as a vessel for storing the diluting fluid RS4. The diluting fluid chamber 14 is charged with, for example, 400 µL, of the diluting fluid RS4. The cleaning fluid chamber 15 is a chamber for charging a cleaning fluid RS5 for cleaning a tip 17. The cleaning fluid chamber 15 is charged with, for example, 400 µL, of the cleaning fluid RS5. The tip 17 is used for transferring the sample S, the color reagent solution RS1 and the diluting fluid RS4 from the respective chambers into which these have been charged to other chambers, and for stirring these fluids when they are mixed together. The tip loading station 16 is a place for loading and holding the tip 17. The tip loading station 16 is also used as a waste fluid chamber where fluids that are no longer needed are discarded.

Color Reagent Solution

The color reagent solution RS1 that has been charged into the color reagent solution chamber 11 is a liquid reagent obtained by dissolving an oxidative color reagent in a solvent. Water, for example, is used as the solvent. In the color reagent solution RS1, the concentration of oxidative color reagent is adjusted so as to ultimately become from 0.2 to 8 mM or from 0.4 to 6.4 mM within the measurement fluid RS2. The oxidative color reagent, upon oxidizing, forms a chromophoric group within the molecule, thereby exhibiting a color. Hence, the concentration of the oxidative color reagent within the color reagent solution RS1 is adjusted to, for example, from 0.24 mM to 9.6 mM or from 0.48 mM to 7.68 mM. The oxidative color reagent, upon oxidizing, becomes a semi-quinone dye or a quinone dye and undergoes coloration. A phenylenediamine derivative is used as the oxidative color reagent. The use of a p-phenylenediamine derivative is especially preferred. The p-phenylenediamine derivative is most preferably a compound represented by general formula (I) below, or a salt thereof.

[Chem. 1]

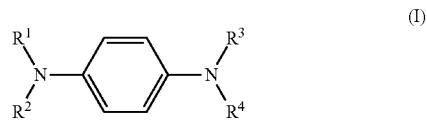

(I)

In general formula (I), $R^1$, $R^2$, $R^3$ and $R^4$ are each independently a hydrogen atom, a methyl group, an ethyl group, an isopropyl group, a hydroxyalkyl group of 1 to 4 carbons, a phenyl group or a halogen group. Examples of the hydroxyalkyl group of 1 to 4 carbons include hydroxymethyl groups, hydroxyethyl groups and hydroxypropyl groups. An example of a hydroxyethyl group is 2-hydroxyethyl group.

In particular, in general formula (I), at least one of $R^1$, $R^2$, $R^3$ and $R^4$ is a methyl group, an ethyl group, an isopropyl group, a hydroxyalkyl group of 1 to 4 carbons, a phenyl group or a halogen group.

Alternatively, two or more of $R^1$, $R^2$, $R^3$ and $R^4$ are each independently a methyl group, an ethyl group, an isopropyl group, a hydroxyalkyl group of 1 to 4 carbons, a phenyl group or a halogen group. Particularly in cases where two or more of $R^1$, $R^2$, $R^3$ and $R^4$ are each independently an isopropyl group, a hydroxyalkyl group of 1 to 4 carbons or a phenyl group, there may be two or more of the same group or two or more may each be differing groups.

Alternatively at least one of $R^1$, $R^2$, $R^3$ and $R^4$ is a phenyl group, and at least one of $R^1$, $R^2$, $R^3$ and $R^4$ is a hydroxyalkyl group of 1 to 4 carbons. In this case, in the compound represented by general formula (I), the nitrogen atom to which the phenyl group is bonded and the nitrogen atom to which the hydroxyalkyl group is bonded may be the same or may be different.

In cases where the p-phenylenediamine derivative of general formula (I) is a compound having, of the above substituents $R^1$ to $R^4$, a substituent other than a phenyl group as any of $R^1$ to $R^4$, this may be the salt of a compound represented by general formula (I). Illustrative examples of such salts include hydrochlorides, sulfates, oxalates and acetates.

Alternatively, the p-phenylenediamine derivative is a compound wherein, in general formula (I), $R^1$ is a hydrogen atom, $R^2$ is a hydrogen atom or an isopropyl group, $R^3$ is a hydrogen atom, an ethyl group or a hydroxyalkyl group of 1 to 4 carbons, and $R^4$ is a hydroxyalkyl group of 1 to 4 carbons or a phenyl group. Such a p-phenylenediamine derivative includes hydrochlorides, sulfates, oxalates, acetates and other salts of compounds wherein, in general formula (I), $R^1$ is a hydrogen atom, $R^2$ is a hydrogen atom, $R^3$ is an ethyl group or a hydroxyalkyl group of 1 to 4 carbons, and $R^4$ is a hydroxyalkyl group of 1 to 4 carbons.

As noted above, p-phenylenediamine derivatives include compounds wherein, in general formula (I), at least one of $R^1$, $R^2$, $R^3$ and $R^4$ is a hydroxyalkyl group of 1 to 4 carbons. p-Phenylenediamine derivatives in which at least one of $R^1$, $R^2$, $R^3$ and $R^4$ is a hydroxyalkyl group of 1 to 4 carbons are highly sensitive as reagents for measuring the degree of oxidative stress and show a sharp absorption. Hence, it is possible with such p-phenylenediamine derivatives to carry out more accurate measurement of the degree of oxidative stress.

Also, as noted above, the p-phenylenediamine derivatives include compounds wherein, in general formula (I), at least one of $R^1$, $R^2$, $R^3$ and $R^4$ is a phenyl group. When at least one of $R^1$, $R^2$, $R^3$ and $R^4$ in the p-phenylenediamine derivative is a phenyl group, although there are differences due to the molecular structure, the color exhibited by oxidation has absorption wavelengths in the broad wavelength region of 420 nm to 800 nm.

Hence, in cases where blood is used as the biological sample for which the degree of oxidative stress is to be measured, by selecting a p-phenylenediamine derivative of the above type which has absorption wavelengths also in a wavelength region on the long wavelength side that is not affected by interference due the presence of blood components such as hemoglobin (the region at wavelengths at and above 600 nm), highly accurate measurement of the degree of oxidative stress becomes possible.

Although the measurement sensitivity sometimes fluctuates depending on, for example, the type of measuring apparatus 2, because this p-phenylenediamine derivative has absorption wavelengths in a broad wavelength region, measurement using such a p-phenylenediamine derivative has the advantage of not being readily subject to sensitivity fluctuations owing to the measuring apparatus 2. In particular, when LEDs are used as the light source for measurement, the measurement sensitivity sometimes fluctuates due to differences between production lots of the LEDs. However, even in such cases, using this p-phenylenediamine derivative makes it possible to more accurately measure the degree of oxidative stress.

When a salt of a compound represented by general formula (I) is used as the oxidative color reagent in this invention, the solubility in a solvent when preparing the color reagent solution increases, which is advantageous for production.

FIG. 3 shows specific examples of p-phenylenediamine derivatives as the oxidative color reagent. Chemical formulas (II) to (X) respectively represent N,N-diethyl-1,4-phenylenediamine (II), N-ethyl-N-(2-hydroxyethyl)-1,4-phenylenediamine (III), N,N-bis(2-hydroxyethyl)-1,4-phenylenediamine (IV), N-isopropyl-N'-phenyl-1,4-phenylenediamine (V), N-phenyl-1,4-phenylenediamine (VI), N-isopropyl-N-phenyl-1,4-phenylenediamine (VII), N-ethyl-N-(2-hydyroxyethyl)-1,4-phenylenediamine sulfate (VIII), N,N-bis(2-hydroxyethyl)-1,4-phenylenediamine sulfate (IX) and N,N-diethyl-1,4-phenylenediamine sulfate (X). However, the oxidative color reagent in this invention is not limited to these.

The color reagent solution RS1 is adjusted so that the hydrogen ion exponent (pH) conditions become strongly acidic. By adding a strong acid and adjusting the hydrogen ion exponent, the color reagent solution RS1 is rendered strongly acidic. The strong acid used may be either a strong inorganic acid or a strong organic acid. Examples of strong inorganic acids include sulfuric acid, hydrochloric acid, nitric acid and phosphoric acid. Examples of strong organic acids include lactic acid, acetic acid, propionic acid, p-toluenesulfonic acid, glycine, phthalic acid, maleic acid, citric acid, succinic acid, oxalic acid and tartaric acid. These may also be used in admixture.

In the color reagent solution RS1, the hydrogen ion exponent is adjusted to strong acidity. As used herein, "strong acidity" refers to a pH below 3.0. Specifically, in the color reagent solution RS1, the hydrogen ion exponent is adjusted so as to be pH 2.9 or below (pH 0 to pH 2.9), pH 2.5 or below (pH 0 to pH 2.5), pH 2.1 or below (pH 0 to pH 2.1), pH 2.0 or below (pH 0 to pH 2.0), pH 1.0 to pH 2.9, pH 1.0 to pH 2.5, pH 1.0 to pH 2.1, pH 1.0 to pH 2.0, or below pH 1.0. The color reagent solution RS1 is adjusted by adding a strong acid while checking the hydrogen ion exponent. In this invention, when adjusting the color reagent solution RS1, the oxidative color reagent may be dissolved after setting the hydrogen ion exponent to strongly acidic, or the oxidative color reagent may first be dissolved in a solvent such as water, and the hydrogen ion exponent then adjusted to strong acidity.

The color reagent solution RS1 may be adjusted to strong acidity by setting the strong acid concentration to a predetermined concentration. In such a case, addition is carried out in such a way that the concentration of the inorganic acid or organic acid becomes one of the following: 0.1 M or more, from 0.0001 mM to 1.0 M, from 0.01 mM to 1.0 M, or from 0.1 M to 1.0 M.

Once such adjustment is complete, the color reagent solution RS1 is charged in an amount of, for example, 200 μL at a time into the color reagent solution chamber 11 of the cartridge 1 shown in FIGS. 1 and 2.

Diluting Fluid

The diluting fluid RS4 is for diluting the sample S. Alternatively, the diluting fluid RS4 is for diluting the color reagent solution RS1. When the sample S is diluted with the diluting fluid RS4, a diluted sample RS3 is formed. The diluted sample RS3 is mixed with the color reagent solution RS1, forming a measurement fluid RS2. Hence, ultimately, the diluting fluid RS4 dilutes the color reagent solution RS1.

The fluid used as this diluting fluid RS4 may be selected from among, for example, acetic acid buffered solutions, phosphate buffered solutions, Tris-maleic acid buffered solutions, citric acid buffered solutions, 2-(N-morpholino)ethanesulfonic acid (MES) buffered solutions, N-(2-acetonamide)iminodiacetic acid (ADA) buffered solutions and Bis-Tris buffered solutions. Of these buffered solutions, an acetic acid buffered solution, an MES buffered solution or a Tris-maleic acid buffered solution is preferred. An acetic acid buffered solution is more preferred.

The hydrogen ion exponent of the diluting fluid RS4 is adjusted to the range of pH 3.6 to pH 5.6 or to the range of pH 4.6 to pH 5.4. The concentration of the buffer included in the diluting fluid RS4 is adjusted so as to ultimately become, in the measurement fluid RS2, from 100 mM to 400 mM or from 200 mM to 400 mM. Hence, the concentration of the buffer is adjusted to, in the diluting fluid RS4, e.g., from 667 mM to 2,667 mM or from 1,333 mM to 2,667 mM. When the color reagent solution is diluted with the diluting fluid RS4, the hydrogen ion exponent of the color reagent solution RS1, owing to the buffering action of the buffer, changes to the hydrogen ion exponent of the diluting fluid RS4.

Once such adjustment is complete, the diluting fluid RS4 is charged in an amount of, for example, 400 μL at a time into the diluting fluid chamber 14 of the cartridge 1 shown in FIGS. 1 and 2.

The color reagent solution RS1 or the diluting fluid RS4 includes a transition metal salt. The transition metal salt is added in order to produce, from the hydroperoxides (R—OOH) included in the sample S, free radicals composed of alkoxy radicals (R—O) and peroxy radicals (R—OO). Examples of the transition metal salt include iron (II) sulfate ($FeSO_4$) and copper (I) sulfate ($Cu_2SO_4$). Of these, iron (II) sulfate is more preferred. The transition metal salt concentration in the color reagent solution RS1 or the diluting fluid RS4 is adjusted so as to ultimately become, in the measurement fluid RS2, from 0.0005 mM to 0.06 mM or from 0.001 mM to 0.03 mM. Therefore, the transition metal salt, when included in the color reagent solution RS1, is adjusted within the range of, for example, from 0.0006 mM to 0.072 mM or from 0.0012 mM to 0.036 mM. When the transition metal salt is included in the diluting fluid RS4, it is adjusted within the range of, for example, from 0.003 mM to 0.4 mM or from 0.007 mM to 0.2 mM.

Tip

As shown in FIGS. 1 and 2, during preparations for measuring the degree of oxidative stress, the tip 17 is mounted on the end of a nozzle 21 (subsequently described) of the measuring apparatus 2 and removed from the tip loading station 16. The tip 17 has the function of, through the operation of a sampling pump unit 21a in the measuring apparatus 2, aspirating and discharging the sample S, the color reagent solution RS1 and the like. The tip 17 can be used in this way to transfer various liquids within the cartridge 1 and to stir by aspiration and discharge. The tip is manufactured from a plastic such as polypropylene or polyethylene.

Measuring Apparatus

The measuring apparatus 2 is for measuring the degree of oxidative stress within an organism using the cartridge 1. As shown in FIGS. 1 and 2, the measuring apparatus 2 is provided with a controller 20, a nozzle 21, a photometric unit 22 and a temperature regulation block 23.

The controller 20 is for controlling operational processing of the measuring apparatus 2. As shown in FIG. 1, the controller 20 is connected via control wires 24 to the sampling pump unit 21a, a nozzle drive unit 21b, the photometric unit 22 and the temperature regulation block 23. The controller 20 has a CPU and a memory. Interface circuits are disposed, as needed, between the CPU and system components such as the sampling pump unit 21a. The CPU controls operational processing of the measuring apparatus 2 by running a program stored in the memory. The memory is provided with a ROM area and a RAM area. The ROM area stores the operational processing program of the measuring apparatus 2, parameters, working curves and the like. The RAM area temporarily stores the operational processing program, etc., and also data acquired by the photometric unit 22. The controller 20 calculates the light absorbance based on this data. The controller 20 uses the working curves stored in the ROM area to calculate, from the absorbance, the hydroperoxide concentration in the sample S, and additionally calculates the degree of oxidative stress. The controller 20 is configured so as to be capable of directly displaying the absorbance.

As shown in FIG. 1, the nozzle 21 is constructed so as to carry out operation by means of the sampling pump unit 21a and the nozzle drive unit 21b. The controller 20 controls the operation of the nozzle 21 by controlling the operation of the sampling pump unit 21a and the nozzle drive unit 21b.

The nozzle 21 is for mounting the tip 17 on the end thereof and dispensing fluid aspirated from a chamber in the cartridge 1 to another chamber, and for the intimate mixture of mixed fluids by aspiration and discharging. The nozzle 21 also has the function of breaking the seal (not shown) that has been attached to the top surface 18 of the cartridge 1 set in the measuring apparatus 2. The nozzle 21 is formed of stainless steel or the like, and is constructed so as to break through and perforate the seal.

After perforating the openings in the chambers, photometric cell and the like needed to measure the degree of oxidative stress, the nozzle 21 inserts the end thereof into the tip 17 that has been loaded into the tip loading station 16 and pulls the tip 17 out of the tip loading station 16. In doing so, the tip 17 becomes mounted on the nozzle 21. The tip 21 is configured so as to, under prompting by the nozzle drive unit 21b, horizontally move over the top surface 18 of the cartridge 1 in the direction indicated by the arrow N1 to a target position and also move vertically in the direction indicated by the arrow N2. The nozzle 21 on which the tip 17 has been mounted, by moving to the position of a target chamber and descending, causes the end of the tip 17 to reach the liquid surface within the chamber. The nozzle 17, under the operation of the sampling pump unit 21a, aspirates the liquid within the chamber of photometric cell up into the tip 17. The nozzle 21 then moves to another target chamber or photometric cell, and dispenses and transfers into these the liquid that was aspirated into the tip 17.

The photometric unit 22 is used to measure coloration of the measurement fluid RS2 within the photometric cell 12. As shown in FIG. 1, the photometric unit 22 has a light-emitting portion 22a and a light-receiving portion 22b. The light-emitting portion 22a and the light-receiving portion 22b are disposed across from one another on either side of the photometric cell 12 when the cartridge 1 has been set within the measuring apparatus 2. The light-emitting portion 22a has LEDs (not shown), and shines light at a wavelength of, e.g., 510 nm, in the direction indicated by the arrow N3. The light-receiving portion 22b has a photodiode (not shown), and receives light that has been emitted by the light-emitting portion 22a and has passed through the photometric cell 12. Control of such light emission and light reception in the photometric unit 22 is carried out by the controller 20.

The temperature regulation block 23 is for regulating the cartridge 1 to a temperature suitable for measuring the degree of oxidative stress. A heater (not shown) is incorporated into the temperature regulation block 23. By controlling the on/off state of this heater, the controller 20 controls the temperature of the cartridge 1 so as to fall within a predetermined range. For example, the controller 20 may control the cartridge 1 to a temperature of 37° C.

Measurement of Degree of Oxidative Stress

An example of the procedure for carrying out measurement of the degree of oxidative stress using the cartridge 1 and the measuring apparatus 2 is described in conjunction with the flow chart shown in FIG. 4. Operation of the measuring apparatus 2 is controlled by the controller 20. In a Reactive Oxygen Metabolites (d-ROMs) test for measuring the degree of oxidative stress, the reactive oxygen/free radicals in an organism are not directly measured. The concentration of hydroperoxide (R—OOH) that has formed as a result of the reactive oxygen/free radicals is measured using a color reaction, and the degree of oxidative stress within the organism is collectively assessed. This is because hydroperoxide (R—OOH) is a general appellation for the lipids, proteins, amino acids, nucleic acids and the like that have incurred oxidizing reactions due to reactive oxygen/free radicals, and serves as a marker of the degree of oxidative stress.

As shown in FIG. 2, the color reagent solution chamber 11, the diluting fluid chamber 14 and the cleaning fluid chamber 15 of the cartridge 1 are respectively filled with specified amounts of the color reagent solution RS1, the diluting fluid RS4 and the cleaning fluid RS5. The operator carrying out the measurement uses a pipette or the like to dispense, for example, 50 μL of a sample in the sample chamber 10. In this example, blood plasma may be used as the sample S. Next, the operator sets the cartridge 1 in the measuring apparatus 2. The operator then closes the lid (not shown) on the measuring apparatus 2 and presses a start button (not shown). After this, the measuring apparatus 2 operates automatically, measuring the degree of oxidative stress.

The nozzle 21 descends as indicated by the arrow in FIG. 2 and mounts on the end thereof the tip 17 that has been loaded into the tip loading station 16 (step S1). The nozzle 21 with the tip 17 mounted thereon moves between the respective chambers as indicated by the arrow N1, and at each chamber moves vertically as indicated by the arrow N2. The nozzle 21 with the tip 17 mounted thereon moves over the cartridge 1 up to the diluting fluid chamber 14 and aspirates the diluting fluid RS4. Next, the nozzle 21 moves to the diluting chamber 13 and dispenses 126 μL of the diluting fluid RS4 into the diluting chamber 13 (step S2). The nozzle 21 then moves to the sample chamber 10 and aspirates a sample S, after which it moves to the diluting chamber 13 and dispenses 14 μL of the sample S to the diluting chamber 13 (step S3). Next, the nozzle 21 moves to the cleaning fluid chamber 15, where it aspirates and discharges cleaning fluid RS5, thereby cleaning the end and interior of the tip 17 (step S4).

The diluting fluid RS4 is an acetic acid buffered solution and is adjusted to a hydrogen ion exponent of pH 5.0. The hydrogen ion concentration of the sample is thereby stabilized. In addition, iron (II) sulfate ($FeSO_4$) is included as a transition metal salt in the measurement fluid RS2 to an ultimate concentration within the measurement fluid RS2 of 0.03 mM. The concentration of transition metal salt in the diluting fluid RS4 is thereby adjusted to, for example, 0.2 mM. Due to the action of the transition metal salt, free radicals made up of alkoxy radicals (R—O) and peroxy radicals (R—OO) arise from the hydroperoxides (R—OOH) that formed in the process of oxidation within the organism.

Next, the nozzle 21 moves to the position of the color reagent solution chamber 11 and aspirates the color reagent solution RS1, after which it dispenses 150 μL of the color reagent solution RS1 into the photometric cell 12 (step S5). Next, the nozzle 21 moves to the diluting chamber 13 and aspirates the diluted sample RS3, then moves to the position of the photometric cell 12 and dispenses 30 μL of the diluted sample RS3 to the photometric cell 12 (step S6). This brings the amount of measurement fluid RS2 to 180 μL. The nozzle 21 stirs, by aspiration and discharging, the measurement fluid RS2 obtained by mixture of the color reagent solution RS1 and the diluted sample RS3 in the photometric cell 12 (step S7). The temperature regulation block 23 holds the photometric cell 12 at a temperature of 37° C. for 5 minutes. Next, the photometric unit 22 measures the absorbance at 510 nm (step S8). Using a working curve determined beforehand, the controller 20 calculates the hydroperoxide concentration from the absorbance (step S9). The controller 20 ultimately calculates the degree of oxidative stress from this hydroperoxide concentration.

N,N-bis(2-hydroxyethyl)-1,4-phenylenediamine sulfate is dissolved in the color reagent solution RS1. This has been made strongly acidic by the addition of, for example, sulfuric acid. Once the diluted sample RS3 containing an acetic acid buffered solution has been added, the hydrogen ion exponent of the measurement fluid RS2 changes to pH 5.0, which is suitable for the color reaction. When this oxidative color reagent comes into contact with free radicals within the photometric cell 12, depending on the amount of free radicals, the reagent changes to radical cations, exhibiting a red-violet color. The intensity of the red-violet coloration reflects the hydroperoxide concentration within the blood and is directly proportional to the reactive oxygen metabolites (ROMs) that are by-products of cells and molecules which have incurred the influence of reactive oxygen/free radicals.

In cases where whole blood is measured as the sample S, a compound in which at least one of $R^1$, $R^2$, $R^3$ and $R^4$ in general formula (I) is a phenyl group can be used as the oxidative color reagent. As noted above, in cases where coloration occurs due to the oxidation of an oxidative color reagent having this structure, a dye having an absorption wavelength in the broad wavelength region of 420 nm to 800 nm forms. This enables measurement at a measurement wavelength which avoids hemoglobin absorption. Wavelengths of, for example, 600 nm or more are employed as this measurement wavelength.

As noted above, in this embodiment, the color reagent solution RS1 has been rendered strongly acidic. Because the dissolved oxidative color reagent such as a p-phenylenediamine derivative is thereby stabilized, a background rise in the color reagent solution RS1 in which the oxidative color reagent has been dissolved can be suppressed. At this time, the reactivity of the oxidative color reagent is maintained without deterioration. It therefore becomes possible to prepare, transport and store the oxidative color reagent as a liquid reagent. The task of dissolving the oxidative color reagent in the solvent just prior to measuring the degree of oxidative stress is thereby eliminated, which is convenient for the operator carrying out the measurement. Moreover, measurement data of a high accuracy can be rapidly obtained.

When an automated instrument is used for measurement, the specifications sometimes call for the automated instrument to run the operation of dissolving the dry oxidative color reagent in a solvent such as water just prior to measurement of the degree of oxidative stress. In such an automated instrument, fully carrying out re-dissolution of the dry oxidative color reagent is an important factor for ensuring the accuracy of measurement. However, there are cases where the measurement accuracy worsens because dissolution of the dry oxidative color reagent is not fully carried out by the automated instrument. In this embodiment, dissolution of the dry oxidative color reagent by the measuring apparatus 2 is not necessary, thereby reducing the burden on the measuring apparatus 2. This can also help to reduce production costs for the measuring apparatus 2. Moreover, because the color reagent solution RS1 in which the oxidative color reagent is completely dissolved can be used directly without modification, a high level of measurement accuracy can be maintained. Hence, the color reagent solution RS1 of this embodiment is suitable for use in a measuring apparatus 2 which automatically carries out measurement of the degree of oxidative stress.

The production of a dry reagent such as a freeze-dried reagent requires, for example, dispensing equipment which accurately dispenses a solution in which the oxidative color reagent is dissolved, or freeze-drying equipment. In this embodiment, because the oxidative color reagent can be prepared, transported and stored as a liquid reagent, when manufacturing the cartridge 1 for measurement of the degree of oxidative stress, there is no need for special dispensing equipment or drying equipment. As a result, the production costs of the cartridge 1 for measuring the degree of oxidative stress can be reduced.

The cartridge 1 additionally includes a diluting fluid RS4 for diluting the color reagent solution RS1. The diluting fluid RS4 is adjusted with a buffer to a predetermined hydrogen ion exponent suitable for the color reaction. Hence, owing to dilution with the diluting fluid RS4, the hydrogen ion exponent of the color reagent solution RS1 that has been adjusted so as to be strongly acidic is made to change to the hydrogen ion exponent of the diluting fluid RS4. As a result, it is possible to accurately measure the degree of oxidative stress.

This invention is not limited to the foregoing embodiment. Various changes may be made to the specific arrangement of steps in the method of suppressing a rise in the background of the color reagent solution according to this invention. Similarly, various design changes may be made to the specific constitution of the color reagent solution, the reagent kit, and the measuring apparatus that uses this reagent kit according to the invention.

In this invention, the reagent kit is not limited to a cartridge 1 having a plurality of chambers and a photometric cell. The reagent kit here encompasses also reagent kits in which the following have been paired as a set: a vessel filled with a strongly acidic color reagent solution in which an oxidative color reagent has been dissolved and, for diluting a sample S, a diluting fluid RS4 in which a transition metal salt has been dissolved.

Also, in this invention, the measuring apparatus is not limited to a measuring apparatus 2 for measuring a cartridge 1. Also included are measuring apparatuses which aspirate a reagent from a bottle, dispense the reagent into a photometric cell prepared as a separate body from the bottle, and measure changes in coloration.

Moreover, in this invention, the oxidative color reagent is not limited to phenylenediamine derivatives. The oxidative color reagent also includes benzidine derivatives such as tetramethylbenzidine and o-tolidine. Trinder's reagent and phenothiazine derivatives are also included in the oxidative color reagent.

EXAMPLES

The advantageous effects of the invention are illustrated more fully below by way of examples. However, the invention is in no way limited by these examples.

Example 1

Comparative Color Reagent Solutions (1) and (2) and Color Reagent Solutions (1) and (2) were prepared in accordance with the formulations shown in FIG. 5. Color Reagent Solutions (1) and (2) were made strongly acidic by the addition of sulfuric acid. N,N-Bis(2-hydroxyethyl)-1,4-phenylenediamine sulfate or N-ethyl-N-(2-hydroxyethyl)-1,4-phenylenediamine sulfate was used as the oxidative color reagent. The sulfuric acid concentration in Color Reagent Solutions (1) and (2) was set to 0.1 M. Aside from not adding sulfuric acid, Comparative Color Reagent Solutions (1) and (2) were given the same compositions as Color Reagent Solutions (1) and (2).

After checking the coloration immediately following preparation of each reagent solution, the solutions were held at 40° C. for 14 days and the degree of background coloration was visually compared. A stronger coloration indicates a larger background rise.

As shown in FIG. 6, immediately after preparation, Comparative Color Reagent Solutions (1) and (2) and Color Reagent Solutions (1) and (2) were all clear and appeared the same. After 14 days of storage at 40° C., Comparative Color Reagent Solutions (1) and (2) both showed a strong violet coloration. By contrast, Color Reagent Solutions (1) and (2) were each slightly pink or clear. This showed that a rise in background is suppressed when stored under strong acidity.

Example 2

Comparative Color Reagent Solution (3) and Color Reagent Solutions (3) to (8) were prepared according to the formulations shown in FIG. 7. N,N-Bis(2-hydroxyethyl)-1,4-phenyelnediamine sulfate was used as the oxidative color reagent. The concentration of the oxidative color reagent was set to 3.2 mM. Sulfuric acid, hydrochloric acid, lactic acid, acetic acid, propionic acid and p-toluenesulfonic acid were used as the strong acids. By adding these strong acids, the hydrogen ion exponents of the respective color reagent solutions were adjusted as shown in FIG. 7. Each color reagent solution was stored at 40° C., and the background coloration was measured immediately after preparation and on days 3 and 7 after preparation. Measurements for each of Color Reagent Solutions (3) to (8) were carried out separately by dispensing the solution in the photometric cell 12 of a cartridge 1 and setting the measuring apparatus 2 so that the absorbance at 510 nm can be displayed. Aside from not adding a strong acid, measurement of the Comparative Color Reagent Solution (3) was carried out under the same conditions as for Color Reagent Solutions (3) to (8).

The results are shown in FIGS. 8 to 13. FIGS. 8 to 13 compare the results for each of Color Reagent Solutions (3) to (8) with the results for Comparative Color Reagent Solution (3). In each graph, the ordinate represents the absorbance at 510 nm and the abscissa represents the number of days stored at 40° C. A larger change in absorbance indicates a larger rise in the background. The graphs of the respective color reagent solutions show the same tendency, regardless of the type of strong acid. That is, there was a discernible trend: regardless of the type of strong acid, the degree of rise in the background becomes smaller when the storage conditions entail a lower hydrogen ion exponent.

A precondition of the cartridge of the invention is that it be stored under refrigerated conditions (4° C. or below). In refrigerated storage, the storage stability is expected to be overwhelmingly better than storage at 40° C. In cases where refrigerated storage is assumed, from the comparisons with Comparative Color Reagent Solution (3), it was confirmed that the background coloration can be suppressed for a relatively short period at a pH of 2.9 or below. By setting the conditions to pH 2.1 or below, it was confirmed that a background rise can be suppressed even in long-term storage.

Example 3

Figures 14, 15:
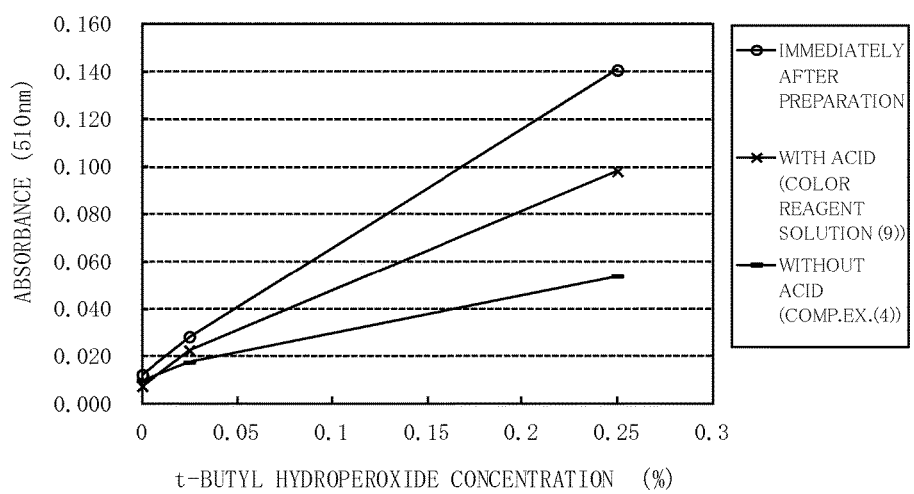
FIG. 14 is a table showing the formulation used in Example 3.
FIG. 15 is a graph showing the confirmatory results obtained in Example 3.

Comparative Color Reagent Solution (4) and Color Reagent Solution (9) were prepared in accordance with the formulation shown in FIG. 14. N,N-Bis(2-hydroxyethyl)-1,4-phenyelendiamine sulfate was used as the oxidative color reagent. In Color Reagent Solution (9), the concentration of the oxidative color reagent was set to 3.2 mM. p-toluenesulfonic acid was used as the strong acid. The concentration of p-toluenesulfonic acid in Color Reagent Solution (9) was adjusted to 0.1 M. Aside from not adding a strong acid, Comparative Color Reagent Solution (4) was set to the same conditions as for Color Reagent Solution (9).

Comparative Color Reagent Solution (4) and Color Reagent Solution (9) were stored at 40° C. for 14 days, and the reactivities immediately after preparation and after storage were compared.

At the time of measurement, an aqueous solution of t-butylperoxide (t-BuOOH) was used as the sample S. t-Butyl peroxide can be used as the standard substance for hydroperoxides (R—OOH). The t-Butyl peroxide solution was adjusted to final concentrations (wt %) in the measurement fluid RS2 of 0%, 0.025% and 0.25%.

The diluting fluid RS4 was adjusted so that, in the final measurement fluid RS2, the concentration of the acetic acid buffered solution (pH 5.0) becomes 300 mM and the concentration of FeSO₄ becomes 0.03 mM. To this end, the concentration of the acetic acid buffered solution (pH 5.0) was adjusted to 2,000 mM, and the FeSO₄ concentration in the acetic acid buffered solution (pH 5.0) was adjusted to 0.2 mM.

Measurement was carried out using Measurement System A and in accordance with the measurement flow diagram shown in FIG. 4. At this time, the measuring apparatus 2 was set so as to enable the absorbance at 510 nm to be displayed.

That is, the color reagent solution chamber 11 and the diluting fluid chamber 14 of the cartridge 1 were filled with, respectively, specified amounts of the color reagent solution (9) and the acetic acid buffering solution. In addition, 50 μL of the above t-butyl peroxide solution was dispensed into the sample chamber 10. Next, the cartridge 1 was set in the measuring apparatus 2 and measurement was started. The nozzle 21 of the measuring apparatus 2 had the tip 17 mounted on the end thereof, and dispensed 126 μL of the acetic acid buffering solution from the diluting fluid chamber 14 to the diluting chamber 13. Next, the nozzle 21 aspirated the t-butyl peroxide solution of sample chamber 10, and dispensed 14 μL of this to the diluting chamber 13.

The nozzle 21 subsequently aspirated the color reagent solution (9) in the color reagent solution chamber 11, and dispensed 150 μL of this to the photometric cell 12. Next, the nozzle 21 aspirated the diluted sample RS3 composed of the t-butyl peroxide solution and the acetic acid buffered solution from the diluting chamber 13, and dispensed 30 μL of this diluted sample RS3 to the photometric cell 12. The nozzle 21 stirred the liquid within the photometric cell 12 by aspiration and discharge, thereby rendering the mixed liquid into measurement fluid RS2. Next, the temperature regulation block 23 held the photometric cell 12 at 37° C. for 5 minutes, and the photometric unit 22 measured the absorbance at 510 nm.

Measurement was carried out in the same way for Comparative Color Reagent Solution (4) as well.

The measurement results are shown in FIG. 15. In the graph, the ordinate represents the absorbance at 510 nm, and the abscissa represents the concentration of t-butyl peroxide. When p-toluenesulfonic acid was added to the color reagent solution RS1, thus rendering the latter strongly acidic, the color reagent solution RS1 had a high absorbance and also had a good reactivity even after storage. That is, it was found that, in Color Reagent Solution (9) which was made strongly acidic, compared with the Comparative Color Reagent Solution (4) which was not strongly acidic, background coloration is suppressed and the reactivity of the oxidative color reagent is retained.

As described above, this invention shows that a color reagent solution RS1 in which an oxidative color reagent has been dissolved can be transported and stored while suppressing a background rise.

What is claimed is:

1. A color reagent solution, comprising an oxidative color reagent of:

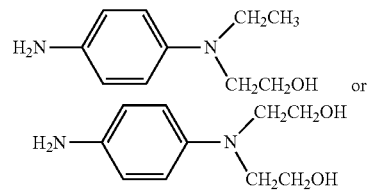

or a salt thereof,
wherein:
the color reagent solution is at a pH of lower than 2.0 and is capable of measuring a component of a sample where the component is a marker of a degree of oxidative stress of the sample; and
the degree of oxidative stress of the sample is reflected by a degree of coloration of the color reagent solution.

2. A reagent kit comprising the color reagent solution according to claim 1.

3. The reagent kit according to claim 2, further comprising a diluting fluid for diluting the color reagent solution, the diluting fluid being at a predetermined pH suitable for a color reaction, and
wherein the pH of the color reagent solution changes to the predetermined pH of the diluting fluid upon treatment of the color reagent solution with the diluting fluid.

4. The color reagent solution according to claim 1, wherein the oxidative color reagent is

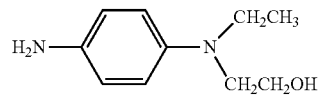

or a salt thereof.

5. The color reagent solution according to claim 1, wherein the oxidative color reagent is

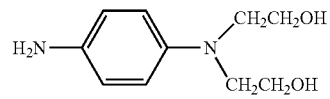

or a salt thereof.

6. The color reagent solution according to claim 1, wherein the color reagent solution is at a pH of lower than 1.0.

7. The color reagent solution according to claim 1, wherein the oxidative color reagent is present in a concentration of 0.2 to 8 mM.

8. The color reagent solution according to claim 1, wherein the component is a hydroperoxide.

9. The color reagent solution according to claim 1, wherein the sample is selected from the group consisting of whole blood, blood plasma, blood serum, urine, saliva, and interstitial fluid.

* * * * *